United States Patent [19]

Maggio et al.

[11] 4,233,402
[45] Nov. 11, 1980

[54] REAGENTS AND METHOD EMPLOYING CHANNELING

[75] Inventors: Edward T. Maggio, Redwood City, Calif.; Richard L. Wife, Sittingbourne, England; Edwin F. Ullman, Atherton, Calif.

[73] Assignee: Syva Company, Palo Alto, Calif.

[21] Appl. No.: 893,650

[22] Filed: Apr. 5, 1978

[51] Int. Cl.² ............................................. C12Q 1/66
[52] U.S. Cl. ..................................... 435/7; 23/230 B; 424/7; 424/12
[58] Field of Search ................. 195/103.5 A, 103.5 R, 195/103.5 M; 23/230 B; 424/7, 12; 435/7, 34

[56] References Cited

U.S. PATENT DOCUMENTS

| | | | |
|---|---|---|---|
| 3,817,837 | 6/1974 | Rubenstein et al. | 195/103.5 A |
| 3,852,157 | 12/1974 | Rubenstein et al. | 195/103.5 A X |
| 4,080,264 | 3/1978 | Cohen et al. | 195/103.5 A |
| 4,104,029 | 8/1978 | Maier, Jr. | 23/230 B |

OTHER PUBLICATIONS

Klaus Mosbach and Bo Mattiasson, Matrix Bound Enzymes, Acta Chemica Scandinavia, vol. 24, pp. 2093–2100, 1970.
Bo Mattiasson and Klaus Mosbach, Studies on a Matrix-Bound Three-Enzyme System, Biochem. Biophys Acta., vol. 235, pp. 253–257, 1971.
Paul A. Srere, Bo Mattiasson and Klaus Mosbach, Proc. Nat. Acad. Sci. USA, vol. 70, No. 9, pp. 2534–2538, 1973.
Dimiter Petkon et al., European Journal of Biochemistry, vol. 51, pp. 25–32, 1975.
James C. Bouin et al., Biochimida et Biophysica Acta., vol. 438, pp. 23–36, 1976.
F. F. Nord, Editor, Advances in Enzymology, vol. 34, pp. 445–536, 1971.
Rachel Goldman et al., Journal of Theoretical Biology, vol. 32, pp. 243–257, 1971.
Charles F. A. Bryce et al., Journal of Biochemistry, vol. 153, pp. 571–577, 1976.

Primary Examiner—Robert J. Warden
Attorney, Agent, or Firm—Bertram I. Rowland

[57] ABSTRACT

Method and compositions are provided for chemical analysis of an analyte which is a member of a specific binding pair of organic substances consisting of ligand and ligand receptor (antiligand). The method involves bringing together the following reagents with the analyte in an aqueous assay medium under mild conditions.

The first reagent is a conjugate of a member of the specific binding pair with a chemical entity which provides a means for chemically changing the concentration of a compound which acts as a signal mediator. The second reagent is the signal mediator precursor. The third reagent is a conjugate of a member of the specific binding pair with a component of a signal producing system of which system the signal mediator is a member.

The amount of signal which can be detected is affected by the local concentration of the signal mediator. By bringing the reagents together in the presence of analyte, where the signal mediator concentration changing means is brought together in a microenvironment with the conjugated signal producing system component, localized concentrations of the signal mediator can be created which differ from the gross concentration of the signal mediator in the assay medium. The degree to which the signal mediator concentration changing means is in close proximity to the signal producing means in a microenvironment will affect the observed signal. By appropriate choice of the two conjugates in conjunction with the analyte, the observed signal can be related to the amount of analyte in the medium.

Novel conjugates are provided, as well as combinations of conjugates in specific proportions to substantially optimize the assay sensitivity. The combinations are provided as kits, where ancillary reagents can also be included, so as to simplify the combination of reagents, as well as provide for more accurate measurements and relative proportions of reagents.

44 Claims, No Drawings

REAGENTS AND METHOD EMPLOYING CHANNELING

BACKGROUND OF THE INVENTION

1. Field of the Invention

The ability for a large organic compound to specifically bind to a spatial and polar structure, an epitopic site, is the basis for a broad spectrum of analytical techniques referred to as competitive protein binding assays. These techniques are predicated on labelling an analyte which provides a detectable signal. The binding of the labelled analyte to its reciprocal member of a specific binding pair allows for discrimination between the labelled analyte bound to the reciprocal member and unlabelled analyte. By allowing for a competition in an assay medium between the analyte in the sample and labelled analyte for the reciprocal binding pair member, one can then determine the amount of analyte in the medium.

A wide variety of labels have been employed, including radioactive atoms, stable free radicals, enzymes and fluorescers. The systems may be illustrated in Murphy, J. Clin. Endocr. 27,973 (1967) and U.S. Pat. Nos. 3,690,834, 3,817,837 and 3,996,345 respectively.

Despite the sensitivity and accuracy of the many systems which are presently available, it is still desirable to provide new systems which have one or more advantages over presently available systems. Advantages include enhanced sensitivity, diminished interference from materials normally present in the medium containing the analyte, ease of manipulation, simplicity of instrumentation, and the like.

2. Description of the Prior Art

Mossbach and Mattiason, Acta Chem. Scand. 24, 2,093 (1970); BBA 253, 253 (1971) teach enhancement of rates when binding two or more enzymes to supports, where the product of the first enzyme is the substrate of the second enzyme. Similar studies have been reported by Srere et al, BNAS 70, 2,534 (1973), Hervagault, et al, Eur. J. Biochem. 51, 19 (1975) and Bouin et al, BBA 438, 23 (1976). The various enzyme combinations employed include hexokinase with glucose-6-phosphate dehydrogenase, malate dehydrogenase with citrate synthetase and pyruvate dehydrogenase; xanthine oxidase with uricase and glucose oxidase with catalase. Katichalski et al, in two papers: Adv. Enzymol. 34, 444 (1971) and J. Theo. Biol., 32, 243 (1971), discuss the phenomenon of "channeling". See also, Bryce et al, Biochem. J. 153, 571 (1976).

SUMMARY OF THE INVENTION

Method and compositions are provided for determining an analyte which is a member of a specific binding pair. The method is predicated on having two means: a first means or first chemical system, frequently involving a single entity, chemically modifies the concentration of a compound in solution, which is referred to as a signal mediator. The second means or second chemical system is a chemical system which is a signal producing means, the nature or amount of signal being affected by the concentration of the signal mediator in its vicinity. The signal producing means has more than one component, the signal mediator and signal producing components being members of the signal producing means.

The first means, the concentration modifying means, is conjugated to a member of the specific binding pair. The first means will normally be a single entity or have one major component e.g. catalyst. It is the major component which is conjugated and will be generally referred to as the first means. A component of the second means, the signal producing means, is also conjugated to a member of the specific binding pair, which may be the same or a different molecule from the molecule to which the concentration modifying means is conjugated. By appropriate choice of the members of the specific binding pair which are conjugated to the components of the first and second means, the amount of analyte in the medium affects the average proximity in which the two means are located in solution. That is, complexes will be formed between reciprocal members of a specific binding pair. Where two or more members in the complex are conjugated to component members of the two means, on the average, the proximity of the two means in the solution will be greatly enhanced. Thus, the first means, the concentration modifying means, is able to affect the concentration of the signal mediator in a restricted environment in the locale of the second means. Since the signal produced by the signal producing means is affected by the localized concentration of the signal mediator, the intensity or amount of signal produced in the complex will differ from the intensity or amount of signal produced in the mass of the solution. The amount of analyte present in the assay medium will affect the degree to which the two means are encompassed in a restricted microenvironment, so that varying amounts of analyte result in varying signal intensity. By employing standards having known amounts of analyte, a signal-concentration relationship may be developed, so that the concentration of analyte may be quantitatively determined.

Conjugate compositions are provided, particularly in the form of kits, where premeasured amounts of the conjugates are included to substantially optimize the sensitivity of the system as well to provide for accurate measurements of reagents and auxiliary materials.

DESCRIPTION OF THE SPECIFIC EMBODIMENTS

Method and compositions are provided for chemical analysis for the determination of organic analytes which are members of a specific binding pair. The specific binding pairs are composed of ligand and ligand receptor, where the ligand receptor recognizes at least one polar and spatial organization of the ligand, namely an epitopic site. The property of a ligand and ligand receptor to specifically bind together, so as to be in close proximity, is employed to create a microenvironment where a detectable signal is substantially modified depending upon whether the elements of the system are in a partially enclosed microenvironment or freely migrating in solution.

The system has three essential or primary elements or reagent systems. The first element acts to affect the concentration of the second element. The first element is a reactive species which reacts with a compound in solution to produce the compound which interacts with the third element. The third element is a signal producing system, which has more than one component, whose signal varies depending upon the localized concentration of the second element, which acts as a member of the system. To the extent that the first and third elements can be brought together in a microenvironment where the concentration of the second element will vary from its concentration in the remainder of the solution, a varying result can be obtained depending upon the number and nature of the microenvironments which are created in solution. By conjugating the first element (reactive element) and a component of the third element (signal producing system) to members of the specific binding pair, a plurality of the first and third elements will be brought together into a substantially fixed spatial relationship when binding occurs. The degree to which the binding of the conjugates occurs to provide for their close proximity will be dependent upon the amount of analyte in solution. Thus, the observed signal will be a function of the amount of analyte in the assay medium.

The subject method involves communication between a first element, a reactive species, which communicates with a third element, a signal producing system by means of a second element, frequently a small compound, either organic or inorganic. The intensity or amount of signal is affected by the concentration of the second element in the environs of the third element.

In the absence of physical restrictions to diffusion in solution, such as porous gels, by the nature of the diffusion processes in solution, the greater the localized concentrations of the three elements in a restricted microenvironment, the more the first element (reactive element) is able to enhance the concentration of the second element in the environs of the third element (signal producing system). Therefore, by providing means for bringing the first and third elements into close proximity in a microenvironment, in the present invention by means of members of a specific binding pair, the communication between the first and third elements is greatly enhanced. The signal observed is then related to the proximity of plurality of the first and third elements in a restricted microenvironment. By further providing that the spatial relationship between a plurality of the first and third elements can be affected by the concentration of an analyte, an assay for the analyte can be developed. The participation of the analyte in the combining of the specific binding pair, either in place of or in combination with members of the specific binding pair, affects the average spatial proximity of the first and third elements, and thus their degree of communication by means of the second element.

With porous gels or similar materials, while proximity is still a factor, of equal or greater significance is the spatial relationship of the two means in the areas or channels confined by the porous gel or similar material.

Various conjugates are provided, particularly in combinations or kits, where their relative proportions are predetermined to at least substantially optimize the sensitivity of the assay. In addition, other ancillary materials may be included with the conjugates so as to avoid measuring errors and simplify the agent preparation.

Definitions

Analyte—The compound or composition to be measured, which may be a ligand which is mono-or polyepitopic, antigenic or haptenic, a single or plurality of compounds which share at least one common epitopic site, or a receptor.

Ligand—Any compound for which a receptor naturally exists or can be prepared.

Ligand Analog—a modified ligand which can compete with the analogous ligand for a receptor, the modification providing means to join a plurality of ligand analogs in a single molecule or to provide a means for directing labels to sites on a ligand. The ligand analog will differ from the ligand by more than replacement of a hydrogen with a bond which links the ligand analog to a hub or label.

Poly(ligand analog)—a plurality of ligand analogs joined together covalently, normally to a hub nucleus. The hub nucleus is a polyfunctional material, normally polymeric, usually having a plurality of functional groups e.g. hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Label—a compound which is either directly or indirectly involved with the production of a detectable signal and is bonded, either directly or indirectly, to ligand, ligand analog, or receptor.

There are two different labels in the subject system which fulfill two different functions.

Reactant Label—the reactant label is a compound, capable of conjugation, conveniently a catalyst, which affects the concentration of a compound (signal mediator) either by destroying the compound in solution or by producing such compound from a precursor in solution. Normally, the signal mediator will be produced from a precursor, so that the initial concentration of the signal mediator will be zero or very small.

Signal Producing Label—the signal producing label is a component of a signal producing system which has at least two components, the signal producing label and the signal mediator. The signal producing label is a compound capable of conjugation which acts together with the signal mediator and, as appropriate, ancillary reagents to produce a signal. The observed signal is related to the concentration of the signal mediator, whose concentration is affected by the reactant label; the signal mediator will normally either directly or indirectly provide for a signal. The signal is conveniently the absorption or emission of electromagnetic radiation, usually in the ultraviolet or visible range, but can also be an electrochemical or thermal change, a nephelometric change or the like.

Signal Mediator—the signal mediator is a compound or excited state of a compound which is produced by interaction with the reactant label and is a component of the signal producing system. The signal produced by the signal producing system is a function of the concentration of the signal mediator. The signal mediator can chemically react or electronically react by transferring energy with a component of the signal producing system, usually the signal producing label.

Receptor—any compound or composition capable of recognizing a particular spatial and polar organization of a molecule i.e. epitopic site. Illustrative receptors include naturally occuring receptors, antibodies, enzymes, Fab fragments, lectins and the like. For any specific ligand, the receptor will be referred to as antiligand. the receptor—antiligand—and its reciprocal ligand form a specific binding pair.

Polyreceptor—a plurality of receptors joined together, either covalently or non-covalently, by means of other receptors, linking groups or a hub nucleus, retaining a substantial proportion of receptor binding sites.

Labeled Ligand—ligand having at least one label covalently bonded to it and retaining at least one epitopic site or label having at least one ligand bonded to it, wherein the ligand retains at least one epitopic site. Particularly with haptenic ligand and small labels (<2,000 m.w.) there can be a plurality of labels and a plurality of ligands which are covalently joined to a polyfunctionalized hub nucleus, either water soluble or insoluble, the hub nucleus having been indicated previously. This composition will be referred to as poly(ligand analog)—polylabel. Desirably, when receptor is bound to ligand in a complex, it will not significantly interfere with the functioning of the label.

Included in the category of labeled ligand are macromolecular conjugates which naturally provide microenvironments on a molecular scale. These macromolecules have well defined channels or surface indentations which can serve to define a volume while providing for limited access to the defined (partially enclosed) volume. Illustrative of such macromolecular compositions are Zeolites, porous glass, cross-linked polyacrylamide, Sepharose, and the like. Both ligand and label can be bonded to the macromolecular hub nucleus. These types of hub nuclei will be referred to as porous hubs.

Reactant label conjugate—reactant label covalently bonded, directly or indirectly, to a member of the specific binding pair, there being one or a plurality of the reactant label and/or specific binding pair member in the conjugate.

Signal producing label conjugate—a component of the signal producing system covalently bonded, either directly or indirectly, to a member of the specific binding pair, there being one or a plurality of the component and/or specific binding pair member in the conjugate.

Reactant label—signal producing label conjugate—both reactant label and signal producing label covalently bonded, directly or indirectly, to the same molecule which is a member of the specific binding pair, then being one or a plurality of each of the labels and/or specific binding pair member in the conjugate. In certain instances the reactant label and signal producing label may be the same. With small ligands ($\leq 1000$ m.w.), a hub nucleus will be involved, while with large ligands, a hub nucleus may or may not be involved. Normally, one of the labels will be a catalyst, usually an enzyme, and particularly the reactant label will be a catalyst.

Labeled receptor—receptor having at least one label covalently bonded to it and retaining at least one binding site or label having at least one receptor bonded to it, wherein the receptor retains at least one binding site. There can be a plurality of receptors and/or labels bonded together, particularly through a hub nucleus. Such a composition will be referred to as polyreceptor-polylabel. Desirably, when ligand is bound to receptor in a complex, there will not be significant interference with the functioning of the label.

As in the case of labeled ligand, macromolecular conjugates involving labeled receptor may be employed. (See above)

Complex—the noncovalent binding or association together of at least one of each of the reciprocal members of the specific binding pair, usually at least two of one of the members with at least one of the reciprocal members, so as to create a microenvironment which creates an at least partially enclosed area which may be differentiated from the main body of the solution. The binding together of the members of the specific binding pair results in the bringing together into close spatial proximity of the reactant label and signal producing label in the microenvironment. The microenvironment is an assemblage or association of a plurality of members of the specific binding pair which assemble in channels, which have restricted communication with the main body of the solution. That is, small molecules are restricted in their diffusion within the ambit of the complex. One can envision a number of building blocks of varying sizes and shapes connected together to create a volume having numerous interstices which are restricted in their communication with the main body of the solution.

The complex creates an environment of localized concentrations of the labels and signal mediator which are greater than the mass of the solution with a resulting enhancement of the amount of detectable signal obtained as compared to a solution in which there are no complexes.

ASSAY

The subject assay is carried out in an aqueous, zone at a moderate pH, generally close to optimum assay sensitivity, normally without separation of the assay components or products. The assay zone for the determination of analyte is prepared by employing an appropriate aqueous solution, normally buffered, the unknown sample, which may have been subject to prior treatment, reactant label conjugate, signal producing label conjugate, signal mediator precursor, and all other materials required for the reactant label and the signal producing label for producing a detectable signal, as well as members of the specific binding pair or their analogs, as required.

The presence of antiligand or ligand in the unknown will affect the degree to which the two labels are on the average brought into spatial proximity. Desirably, at least one of the label conjugates should be polyvalent in binding sites, or the ligand or conjugate provided in a form having a plurality of binding sites e.g. poly(ligand analog), so that a relatively large microenvironment may be created, where a plurality of reactant labels and signal producing labels create a community enclosing a volume of solution containing the signal mediator precursor, which volume of solution is restricted in its communication with the remainder of the solution.

The reaction of the signal mediator precursor with the reactant label to produce the signal mediator has the ultimate effect of enhancing the detectable signal. The signal mediator then participates in the signal producing system to produce the detectable signal, where in the absence of the signal mediator the detectable signal is not observed. Since the likelihood of interaction by either collision or energy transfer, between the signal mediator and another component of the signal producing system will be greater in the microenvironment of the complex, an enhancement of the detectable signal will be observed as compared to the mass of the solution.

Therefore, the greater the number of microenvironments where a plurality of the two different labels are in close proximity, the greater will be the enhancement of the signal as a result of the increased concentration of the signal mediator in the microenvironment as compared to the remainder of the solution.

In carrying out the assay an aqueous medium will normally be employed. Other polar solvents may also be employed, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing proficiency. In some instances, a compromise will be made between these two considerations. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally emloyed for carrying out the assay and usually constant temperatures during the period of the assay. The temperatures for the determination will generally range from about 10°–50° C., more usually from about 15°–40° C.

The concentration of analyte which may be assayed will generally vary from about $10^{-4}$ to $10^{-15}$M, more usually from about $10^{-6}$ to $10^{-13}$M. Considerations such as whether the assay is qualitative, semi-quantitative or quantitative, the particular detection technique and the concentration of the analyte of interest will normally determine the concentration of the other reagents.

While the concentrations of the various reagents will generally be determined by the concentration range of interest of the analyte, the final concentration of each of the reagents will normally be determined empirically to optimize the sensitivity of the assay over the range of interest. The total binding sites of the members of the specific binding pair which are reciprocal to the analyte will be not less than about 0.1 times the minimum concentration of interest based on binding sites of the analyte and not more than about 1000 times the maximum concentration of interest based on analyte binding sites, usually about 0.1–100 times, more usually about 0.3–10 times the maximum concentration of interest. For polyepitopic ligand receptor analytes, the equivalent ratio of labelled ligand to receptor analyte will generally be not less than about 0.01 times the minimum concentration of receptor analyte and not greater than 100 times the maximum concentration of receptor analyte in the range of interest. Additional receptor may be included in the assay for receptor analyte. For ligand analyte, where labelled ligand is employed, the concentration range of the labelled ligand based on equivalents will generally be not less than about $10^{-4}$, more usually not less than $10^{-2}$ times the minimum concentration of interest and not greater than 100, usually not greater than 10 times the maximum concentration of interest.

The concentration of signal mediator precursor may vary widely and is not critical above a minimum level generally ranging from about 1 to $10^{-8}$M, usually from about $10^{-2}$ to $10^{-6}$M.

The order of addition of the various reagents may vary widely, depending upon the particular labels, the compound to which the label is conjugated, the nature of the conjugates, the nature of the analyte, and the relative concentrations of the analyte and reagents.

Also, affecting the order of addition is whether an equilibrium mode or rate mode is employed for the determination.

In developing an order of addition, there will be certain basic considerations. The observed signal from the assay is predicated on the formation of a plurality of microenvironments which desirably have a plurality of the two labels, the reactant label and the signal producing label, in close spatial proximity, where the amount of analyte affects the number and nature of the microenvironments. Therefore, the analyte must be able to be involved in the formation of the microenvironments. The requirement that the analyte affect the formation of the microenvironments will normally govern the order of addition.

Since with many receptors, the rate of binding far exceeds the rate of dissociation, one will normally avoid adding analyte after combining ligand and receptor reagents. For example, with an antigenic analyte, where the reactant label is conjugated to the antigen and the signal producing label is conjugated to the receptor, one would normally not combine the two conjugates prior to addition of the analyte. It would be appropriate to add the receptor conjugate to the analyte, followed by the addition of the antigen conjugate or combine the antigen conjugate and antigen analyte together, followed by the addition of the receptor conjugate.

Regardless of the nature of the analyte, all the reagents can be added simultaneously and either a rate or equilibrium determination made. Where monoepitopic ligands are involved, a species must be present which has a plurality of ligand epitopic sites. The species can either be a poly(ligand analog) or a poly(ligand analog)-label or a poly(ligand analog)-polylabel. Where the label is a large molecule, such as an enzyme, a plurality of ligand analogs may be conjugated to the label. Where the label is a small organic molecule e.g. an energy acceptor which will reemit, both the ligand analog and label will be conjugated to a hub nucleus. Regardless of the size of the ligand and the label, both may be conjugated to a hub nucleus.

The reagents can be provided with both labels conjugated to the same or different molecules of ligand, both labels conjugated to the same or different molecules of receptor, or one label conjugated to ligand and the other label conjugated to receptor. In addition, where ligands are the analyte, and the labels are conjugated to ligand, antiligand or poly(ligand analog) will also be added. One can prepare an assay for monoepitopic ligand having small labels, by including in the assay medium poly(ligand analog) and antibody. More preferred would be to employ a poly(ligand analog)-polylabel or poly(ligand analog)-label with a receptor label conjugate. The monoepitopic analyte could then be added to the receptor conjugate, followed by the ligand label conjugate.

For polyepitopic ligand analyte, conveniently two receptor conjugates can be employed which are brought together by the analyte. Alternatively, a competition can be provided between the ligand analyte and ligand label conjugate for receptor label conjugate. The analyte may therefore be added to either one of the conjugates, followed by the addition of the other conjugate, or the three materials added simultaneously.

Similar considerations involve receptor analytes. Usually two ligand label conjugates will be employed or a combination of a ligand label conjugate and receptor label conjugate. Where the two labels are conjugated to receptor, then either poly(ligand analog) or antigen will be included in the assay medium. Conveniently, the two labelled ligands can be combined as a single reagent for the receptor. If labelled receptor is employed, all of the receptors will be added simultaneously to the assay medium.

With both monoepitopic and polyepitopic ligands, the former in conjunction with poly(ligand analog), either wit or without label, polyreceptor may be employed to increase the number of labels which may be brought together into close proximity. With polyreceptor, the reactant label and signal producing label could be conjugated to different molecules of ligand, or the two labels conjugated to reciprocal members of the specific binding pair.

The signal mediator precursor will normally be added to the assay medium in a manner which avoids a significant change in concentration of the signal mediator prior to completing the addition of the other reagents. The signal mediator precursor may therefore be added prior to, at the same time, or subsequent to the analyte and the other reagents. The signal mediator precursor can be conveniently added simultaneously with the reactant label or subsequent to the combination of the analyte and all the other reagents. Again, it is primarily a practical consideration as to the manner of measurement and the affect on the concentration of signal mediator of adding the signal mediator precursor prior to completion of addition to the assay medium of the analyte and other reagents.

One or more incubation steps may be involved in preparing the assay medium. For example, it may be desirable to incubate an antigen analyte with receptor label conjugates. Alternatively, it may be desirable to incubate an antigen analyte with a receptor label conjugate, followed by the addition of an antigen label conjugate with a second incubation. Whether to employ an incubation period and the length of the incubation period will depend to a substantial degree on the mode of determination—rate or equilibrium—and the rate of binding of the receptor to the ligand. Usually, incubation steps will vary from aout 0.5 min to 16 hours, more usually from about 5 min to 1 hour. Incubation temperatures will generally range from about 4° C. to 50° C., more usually from about 15° C. to 37° C.

After the reagents and combined, the signal will then be determined. The method of determination may be the observation of electromagnetic radiation, particularly ultraviolet and visible light, either absorption or emission, gravimetric, volumetric, electrochemically, and the like. Desirably, the signal will be read as electromagnetic radiation in the ultraviolet or visible region, particularly from about 250 to 750 nm.

The temperature at which the signal is observed will generally range from about 10°–50° C., more usually from about 15°–40° C.

Standard assay media can be prepared which have known amounts of the analyte. The observed signals with the standard assay media may then be graphed, so as to relate concentration to signal. Once a standard curve has been established, a signal may be directly related to the concentration of the analyte.

Materials

The components employed in the assay are the analyte, which includes both ligand and receptor, ligand analog, hub nucleus, reactant label, signal producing label, signal mediator precursor, and, as appropriate, ligand or receptor.

Analyte

The ligand analytes of this invention are characterized by being monoepitopic or polyepitopic. The polyepitopic ligand analytes will normally be poly(amino acids) i.e. polypeptides and proteins, polysaccharides, nucleic acids, and combinations thereof. Such combinations or assemblages include bacteria, viruses, chromosomes, genes, mitochondria, nuclei, cell membranes, and the like.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

The wide variety of proteins may be considered as to the family of proteins having similar structural features, proteins having particular biological functions, proteins related to specific microorganisms, particularly disease causing microorganisms, etc.

The following are classes of proteins related by structure:
protamines
histones
albumins
globulins
scleroproteins
phosphoproteins
mucoproteins
chromoproteins
lipoproteins
nucleoproteins
glycoproteins
unclassified proteins, e.g. somatotropin, prolactin, insulin, pepsin A number of proteins found in the human plasma are important clinically and include:
Prealbumin
Albumin
$\alpha_1$-Lipoprotein
$\alpha_1$-Acid glycoprotein
$\alpha_1$-Antitrypsin
$\alpha_1$-Glycoprotein
Transcortin
4.6S-Postalbumin
Tryptophan-poor
   $\alpha_1$-glycoprotein
$\alpha_1\chi$-Glycoprotein
Thyroxin-binding globulin
Inter-$\alpha$-trypsin-inhibitor
Gc-globulin
   (Gc 1-1)
   (Gc 2-1)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)

Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
   (IgG) or $\gamma$G-globulin
Mol. formula:
   $\gamma_2\kappa_2$ or $\gamma_2\lambda_2$
Immunoglobulin A (IgA)
   or $\gamma$A-globulin
Mol. formula:
   $(\alpha_2\kappa_2)^n$ or $(\alpha_2\lambda_2)^n$
Immunoglobulin M
   (IgM) or $\gamma$M-globulin
Mol. formula:
   $(\mu_2\kappa_2)^5$ or $(\mu_2\lambda_2)^5$
Immunoglobulin D(IgD)
   or $\gamma$D-Globulin ($\gamma$D)
Mol. formula:
   $(\delta_2\kappa_2)$ or $(\delta_2\lambda_2)$
Immunoglobulin E (IgE)
   or $\gamma$E-Globulin ($\gamma$E)
Mol. formula:
   $(\epsilon_2\kappa_2)$ or $(\epsilon_2\lambda_2)$
Free K and $\gamma$ light chains
complement factors:
C'1
   C'1q
   C'1r
   C'1s
C'2
C'3
   $\beta_1$A
   $\alpha_2$D
C'4
C'5
C'6
C'7
C'8
C'9

Important blood clotting factors include:

| BLOOD CLOTTING FACTORS | |
|---|---|
| International designation | Name |
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor, plasma thromboplastin component (PTC) |
| X | Stuart-Prower factor, autoprothrombin III |
| XI | Plasma thromboplastin antecedent (PTA) |
| XII | Hagemann factor |
| XIII | Fibrin-stabilizing factor |

Important protein hormones include:
Peptide and Protein Hormones
   Parathyroid hormone (parathromone)
   Thyrocalcitonin
   Insulin
   Glucagon
   Relaxin
   Erythropoietin
   Melanotropin (melanocyte-stimulating hormoe; intermedin)
   Somatotropin (growth hormone)
   Corticotropin (adrenocorticotropic hormone)
   Thyrotropin
   Follicle-stimulating hormone
   Luteinizing hormone (interstitial cell-stimulating hormone)
   Luteomammotropic hormone (luteotropin, prolactin)
   Gonadotropin (chorionic gonadotropin)
Tissue Hormones
   Secretin
   Gastrin
   Angiotensin I and II
   Bradykinin
   Human placental lactogen
Peptide Hormones from the Neurohypophysis
   Oxytocin
   Vasopressin
   Releasing factors (RF) CRF, LRF, TRF, Somatotropin-RF, GRF, FSH-RF, PIF, MIF Other polymeric materials of interest are mucopolysaccharides and polysaccharides.

Illustrative antigenic polysaccharides derived from microorganisms are as follows:

| Species of Microorganisms | Hemosensitin Found in |
|---|---|
| Streptococcus pyogenes | Polysaccharide |
| Diplococcus pneumoniae | Polysaccharide |
| Neisseria meningitidis | Polysaccharide |
| Neisseria gonorrhoeae | Polysaccharide |
| Corynebacterium diphtheriae | Polysaccharide |
| Actinobacillus mallei; Actinobacillus whitemori | Crude extract |
| Francisella tularensis | Lipopolysaccharide Polysaccharide |
| Pasteurella pestis | |
| Pasteurella pestis | Polysaccharide |
| Pasteurella multocida | Capsular antigen |
| Brucella abortus | Crude extract |
| Haemophilus influenzae | Polysaccharide |
| Haemophilus pertussis | Crude |
| Treponema reiteri | Polysaccharide |
| Veillonella | Lipopolysaccharide |
| Erysipelothrix | Polysaccharide |
| Listeria monocytogenes | Polysaccharide |
| Chromobacterium | Lipopolysaccharide |
| Mycobacterium tuberculosis | Saline extract of 90% phenol extracted mycobacteria and polysaccharide fraction of cells and tuberculin |
| Klebsiella aerogenes | Polysaccharide |
| Klebsiella cloacae | Polysaccharide |
| Salmonella typhosa | Lipopolysaccharide, Polysaccharide |
| Salmonella typhi-murium; Salmonella derby Salmonella pullorum | Polysaccharide |

| Species of Microorganisms | Hemosensitin Found in |
|---|---|
| Shigella dysenteriae | Polysaccharide |
| Shigella flexneri | |
| Shigella sonnei | Crude, polysaccharide |
| Rickettsiae | Crude extract |
| Candida albicans | Polysaccharide |
| Entamoeba histolytica | Crude extract |

The microorganisms which are assayed may be intact, lysed, ground or otherwise fragmented, and the resulting composition or portion, e.g. by extraction, assayed. Microorganisms of interest include:

Corynebacteria
    *Corynebacterium diptheriae*
Pneumococci
    *Diplococcus pneumoniae*
Streptococci
    *Streptococcus pyogenes*
    *Streptococcus salivarus*
Staphylococci
    *Staphylococcus aureus*
    *Staphylococcus albus*
Neisseriae
    *Neisseria meningitidis*
    *Neisseria gonorrheae*
Enterobacteriaciae

| | |
|---|---|
| *Escherichia coli* | |
| *Aerobacter aerogenes* | The coliform bacteria |
| *Klebsiella pneumoniae* | |
| *Salmonella typhosa* | |
| *Salmonella choleraesuis* | The Salmonellae |
| *Salmonella typhimurium* | |
| *Shigella dysenteriae* | |
| *Shigella schmitzii* | |
| *Shigella arabinotarda* | |
| | The Shigellae |
| *Shigella flexneri* | |
| *Shigella boydii* | |
| *Shigella Sonnei* | |

Other enteric bacilli

| | |
|---|---|
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |

Hemophilus-Bordetella group

| Hemophilus influenzae, | H. ducreyi |
|---|---|
| | H. hemophilus |
| | H. aegypticus |
| | H. paraiufluenzae |
| *Bordetella pertussis* | |

Pasteurellae
    *Pasteurella pestis*
    *Pasteurella tulareusis*
Brucellae
    *Brucella melitensis*
    *Brucella abortus*
    *Brucella suis*
Aerobic Spore-forming Bacilli
    *Bacillus anthracis*
    *Bacillus subtilis*
    *Bacillus megaterium*
    *Bacillus cereus*
Anaerobic Spore-forming Bacilli
    *Clostridium botulinum*
    *Clostridium tetani*
    *Clostridium perfringens*
    *Clostridium novyi*
    *Clostridium septicum*
    *Clostridium histolyticum*
    *Clostridium tertium*
    *Clostridium bifermentans*
    *Clostridium sporogenes*
Mycobacteria
    *Mycobacterium tuberculosis hominis*
    *Mycobacterium bovis*
    *Mycobacterium avium*
    Mycobacterium leprae
    *Mycobacterium paratuberculosis*
Actinomycetes (fungus-like bacteria)
    *Actinomyces israelii*
    *Actinomyces bovis*
    Actinomyces naeslundii
    *Nocardia asteroides*
    *Nocardia brasiliensis*
The Spirochetes
    *Treponema pallidum*
    *Treponema pertuenue*
    *Treponema carateum*
    *Borrelia recurrentis*
    *Leptospira icterohemorrhagiae*
    *Leptospira canicola*
    *Spirillum minus*
    *Streptobacillus moniliformis*
Mycoplasmas
    *Mycoplasma pneumoniae*
Other pathogens
    i Listeria monocytogenes
    *Erysipelothrix rhusiopathiae*
    *Streptobacillus moniliformis*
    *Donvania granulomatis*
    *Bartonella bacilliformis*
Rickettsiae (bacteria-like parasites)
    *Rickettsia prowazekii*
    *Rickettsia mooseri*
    *Rickettsia rickettsii*
    *Rickettsia conori*
    *Rickettsia australis*
    *Rickettsia sibiricus*
    *Rickettsia akari*
    *Rickettettsia tsutsugamushi*
    *Rickettsia burnetii*
    *Rickettsia quintana*
Chlamydia (unclassifiable parasites bacterial/viral)
    Chlamydia agents (naming uncertain)
Fungi
    *Cryptococcus neoformans*
    *Blastomyces dermatidis*
    *Histoplasma capsulatum*
    *Coccidioides immitis*
    *Paracoccidioides brasiliensis*
    *Candida albicans*
    *Aspergillus fumigatus*
    *Mucor corymbifer* (*Absidia corymbifera*)

| | |
|---|---|
| *Rhizopus oryzae* | Phycomycetes |
| *Rhizopus arrhizus* | |

| -continued |
| --- |
| *Rhizopus nigricans* |

*Sporotrichum schenkii*
*Fonsecaea pedrosoi*
*Fonsecaea compacta*
*Fonsecaea dermatitidis*
*Cladosporium carrionii*
*Phialophora verrucosa*
*Aspergillus nidulans*
*Madurella mycetomi*
*Madurella grisea*
*Allescheria boydii*
*Phialosphora jeanselmei*
*Microsporum gypseum*
*Trichophyton mentagrophytes*
*Keratinomyces ajelloi*
*Microsporum canis*
*Microsporum canis*
*Microsporum andouini*
Viruses
Adenoviruses
Herpes viruses
   Herpes simplex
   Varicella (Chicken pox)
   Herpes Zoster (Shingles)
   Virus B
   Cytomegalovirus
Pox Viruses
   Variola (smallpox)
   Vaccinia
   *Poxvirus bovis*
   Paravaccinia
   *Molluscum contagiosum*
Picornaviruses
Poliovirus
   Coxsackievirus
   Echoviruses
   Rhinoviruses
Myxoviruses
   Influenza (A, B, and C)
   Parainfluenza (1–4)
   Mumps Virus
   Newcastle Disease Virus
   Measles Virus
   Rinderpest Virus
   Canine Distemper Virus
   Respiratory Syncytial Virus
   Rubella Virus
Arboviruses
   Eastern Equine Eucephalitis Virus
   Western Equine Eucephalitis Virus
   Sindbis Virus
   Chikugunya Virus
   Semliki Forest Virus
   Mayora Virus
   St. Louis Encephalitis Virus
   California Encephalitis Virus
   Colorado Tick Fever Virus
   Yellow Fever Virus
   Dengue Virus
Reoviruses
   Reovirus Types 1–3
Hepatitis
   Heptalitis A Virus
   Hepatitis B Virus
Tumor Viruses
Rauscher Leukemia Virus
Gross Virus
Maloney Leukemia Virus
Allergens The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which includes morphine, codeine, heroin, dextromethorphan, their derivatives and metabolites; cocaine alkaloids, which includes cocaine and benzoyl ecgonine, their derivatives and metabolites; ergot alkaloids, which includes the diethylamide of lysergic acid; steroid alkaloids; iminazoyl alkaloids; quinazoline alkaloids; isoquinoline alkaloids; quinoline alkaloids; which includes quinine and quinidine; diterpene alkaloids, their derivatives and metabolites.

The next group of drugs includes steroids, which includes the estrogens, gestrogens, androgens, andrenocortical steroids, bile acids, cardiotonic glycosides and aglycones, which includes digoxin and digoxigenin, saponins and sapogenins, their derivatives and metabolites. Also included are the steroid mimetic substances, such as diethyl stilbestrol.

The next group of drugs is lactams having from 5 to 6 annular members, which include the barbiturates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, their metabolites and derivatives.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, their metabolites and derivatives.

The next group of drugs is the nucleosides and nucleotides, which include ATP, NAD, FNM, adenosine, guanosine, thymidine, and cytidine with their appropriate sugar and phosphate substituents.

The next group of drugs is miscellaneous individual drugs which include methadone, meprobamate, serotonin, meperidine, amitripytline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

The next group of compounds is amino acids and small peptides which include polyiodothyronines e.g. thyroxine, and triiodothyronine, oxytocin, ACTH, angiotensin, met- and leu-enkephalin their metabolites and derivatives.

Metabolites relates to diseased states include spermine, galactose, phenylpyruvic acid, and porphyrin type.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfenamides, their metabolites and derivatives.

For receptor analytes, the molecular weights will generally range from 10,000 to $2\times10^6$, more usually from 10,000 to $10^6$. For immunoglobulins, IgA, IgG, IgE and IgM, the molecular weights will generally vary from about 160,000 to about $10^6$. Enzymes will normally range from about 10,000 to 600,000 in molecular weight. Natural receptors vary widely, generally being at least about 25,000 molecular weight and may be $10^6$ or highr molecular weight, including such materials as avidin, thyroxine binding globulin, thyroxine binding prealbumin, transcortin, etc.

Ligand Analog

The ligand analog will differ from the ligand either by replacement of a hydrogen or a functionality with a bond or a linking group which has a functionality for forming a covalent bond to another molecule having an active functionality, such as an hydroxyl, amino, aryl, thio, olefin, etc., where the resulting compound differs from the ligand by more than substitution of a hydrogen by the molecule to which it is conjugated. The linking group will normally have from 1-20 atoms other than hydrogen, which are carbon, oxygen, sulfur, nitrogen, and halogen of atomic number 17-35. The functionalities which are involved include carbonyl, both oxo and non-oxo, active halogen, diazo, mercapto, ethylene, particularly activated ethylene, amino, and the like. The number of heteroatoms will generally range from about 0-6, more usually from about 1-6, and preferably from about 1-4. A description of linking groups may be found in U.S. Pat. No. 3,817,837, which disclosure is incorporated herein by reference.

For the most part, the linking groups will be aliphatic, although with diazo groups, aromatic groups are involved. Generally, the linking group is a divalent chain having about 1-10, more usually from about 1-6 atoms in the chain. Oxygen will normally be present as oxo or oxy, bonded to carbon and hydrogen, preferably bonded solely to carbon, while nitrogen will normally be present as amino, bonded solely to carbon, or amido, while sulfur would be analgous to oxygen.

Common functionalities in forming the covalent bond between the linking group and the molecule to be conjugated are alkylamine, amide, amidine, thioamide, urea, thiourea, guanidine, and diazo.

Linking groups which find particular application with conjugation to polypeptides are those involving carboxylic acids which may be used in conjuction with diimides, or as mixed anhydrides with carbonate monoesters or as active carboxylic esters e.g. N-hydroxy succinimide or p-nitrophenyl. Nitrogen analogs may be employed as imidoesters. Aldehydes can be used to form imines under reductive amination conditions e.g. in the presence of borohydrides, to produce alkylamines. Other non-oxo carbonyl groups which may be employed include isocyanates and isothiocyanates. In addition, active halide may be employed, particularly bromoacetyl groups.

In most instances, the ligand will have one or more functional groups which may be employed as the site for linking the linking group. Particularly, hydroxy, amino and aryl groups, particularly activated aryl groups find use. Also, oximes may be prepared from oxo functionalities and the hydroxyl used as a site for joining to a linking group, such as carboxymethyl.

The choice of linking group will vary widely, depending upon the functionalities which are present in the ligand, in the compound to which the ligand is to be conjugated, the nature and length of the linking group desired, and the like.

Hub Nucleus

The hub nucleus may vary widely, being either soluble or insoluble in an aqueous medium, preferably soluble or capable of stable uniform dispersion. The hub nucleus must either have a plurality of functionalities to which ligand analog and/or label may be covalently bonded or can be functionalized to provide such capability. The insoluble hub nuclei may be of any shape or dimension or in fact may be a portion of the container. Various materials which may find use include glasses, which may be functionalized with halosilanes, addition and condensation polymers, such as polystyrene, methacrylates, acrylates, polyvinyl, e.g. polyvinyl chloride or acetate, polyolefins, polyterephthalate esters, polyurethanes, and the like.

Soluble hub nuclei will for the most part be comprised of poly(amino acids), polysaccharides, nucleic acids, water soluble addition polymers e g. polyvinyl alcohol, and the like. Illustrative specific materials include albumins, globulins, gelatin, modified cellulose, dextran, starch, carboxymethylcellulose, agar, polylysine, and the like.

The hub nuclei will generally be at least about 30,000 molecular weight, more usually about 50,000 molecular weight, and may be many millions of molecular weight. Usually, there will be at least on the average about one ligand or one receptor and when appropriate one label per $10^7$ molecular weight of the hub molecule, more usually at least about 1 per $10^6$ molecular weight, and most usually at least about 1 per $10^5$ molecular weight, but usually not more on the average than about 1 per 1,500 molecular weight.

The ratio of ligand to label bonded to the hub nucleus may be varied widely depending on the nature of the two molecules, whether the ligand is mono- or polyepitopic, whether the label is a small or large molecule, the sensitivity required for the assay, and the like. Generally, the number ratio will vary in the range of about 0.01 to 100:1 of ligand to label, preferably about 0.05 to 20:1.

Reactant Label

While reactant labels can be employed which can only be involved in a single event, desirably each reactant label should be involved in a plurality of events. The reactant label will react with a compound in solution to either produce or destroy a compound which is able to interact with the signal producing label so as to produce a modulated signal.

The first type of label is catalytic label, which involves both enzymatic and non-enzymatic catalysts. A wide variety of enzymes may be employed which produce a product which can be involved in the production of a signal. The first type of enzymes to be considered is the oxidoreductases. These enzymes under the I.U.B.

classification are Class 1. Of particular interest in this class are the groups of enzymes in 1.1.1 and 1.6, where nicotinamide adenine dinucleotide or its phosphate (NAD and NADP) are involved. These enzymes can be used to produce the reduced form of the coenzyme NADH and NADPH or vice versa. Specific enzymes include the dehydrogenases, such as alcohol dehydrogenase, glycerol dehydrogenase, lactate dehydrogenase, malate dehydrogenase, glucose-6-phosphate dehydrogenase, mannitol-1-phosphate dehydrogenase, glyceraldehyde-3-phosphate dehydrogenase and isocitrate dehydrogenase.

Another group of enzymes in the oxidoreductase class are those that produce or destroy hydrogen peroxide. Among these enzymes are those of group 1.11.1, such as catalase and peroxidase, amono acid oxidase, glucose oxidase, galactose oxidase, uricase, polyphenol oxidase and ascorbate oxidase. Another oxidoreductase enzyme of interest is diaphorase.

Another group of enzymes of interest is the transferases, Class 2 of the I.U.B. classification, particularly subclass 2.7, where phosphate is transferred to an alcohol, Class 2.7.1 e.g. hexokinase.

Another group of enzymes of interest is the hydrolases which are class 3 in the I.U.B. classification. Of particular interest are the glycoside hydrolases (glycosidase), which are in Class 3.2.1 and phosphatases in Class 3.1.3. Of particular interest are alpha-amylase, cellulase, beta-galactosidase, amyloglucosidase, beta-glucuronidase, acid phosphatase and alkaline phosphatase.

Two additional groups of enzymes of inerest are the lyases, in class 4 and the isomerases in Class 5, particularly subclasses 5.3 and 5.4, which include such enzymes as phosphoglucose isomerase, triose phosphate isomerase and phosphoglucose mutase.

As illustrative of the manner of action of the various enzymes, the following examples are given. The first examples are concerned with the oxidoreductases, particularly those reducing NAD to NADH. These enzymes are for the most part dehydrogenases, where an hydroxylic group is taken to an oxo group. NADH then becomes a signal mediator which can be combined with a number of enzymes or nonenzymatic catalysts to produce a product which may be detected. For example, the signal producing label can be diaphorase, which can react with a synthetic substrate, such as 2,6-dichlorophenolindophenol, methylene blue or potassium ferricyanide. The NADH can be employed with a flavoprotein, which includes such enzymes as glucose oxidase, amino acid oxidases and dihydroorotate dehydrogenase, where the product of the flavoprotein and NADH oxygen, namely hydrogen peroxide may then be detected. See below.

Alternatively, a non-enzymatic catalyst may be employed, such as phenazine methosulfate or Meldola blue, with a dye, such as a tetrazolium salt, to produce the signal.

Alternatively, one can use an oxidoreductase which produces hydrogen peroxide. Such enzymes include glucose oxidase, cytochrome reductase, uricase, and the like. These enzymes can be coupled with an enzyme which reacts with hydrogen peroxide, such as a peroxidase, with the hydrogen peroxide reacting as the signal mediator. The hydrogen peroxide, plus the peroxidase, plus a luminescent material e.g. luminol, can be employed for producing a chemiluminescent reaction.

Hydrolases can be effectively used employing compounds, which require the hydrolytic removal of the two substituents in two separate steps.

For example, 1-umbelliferyl-$\beta$-galactoside-6-phosphate must be converted to umbelliferone in order to obtain a fluorescent signal. By employing alkaline phosphatase as the reactant label, 1-umbelliferyl-$\beta$-galactoside as the signal mediator, and $\beta$-galactosidase as the signal producing label, one can obtain a detectable signal-fluorescence-which will be dependent upon the proximity of the two labels in a complex. Body enzymes are essential to the formation of umbelliferone which provides the detectable signal.

Alternatively, the hydrolase may produce a product which may then be used in a subsequent enzymatic or nonenzymatic reaction. For example, a coenzyme may be functionalized so as to inhibit its activity and the functionality be removable by a hydrolase enzyme and the free coenzyme then able to interact with the signal producing enzyme to produce a detectable signal.

In addition, isomerases can be used to produce a substrate for a subsequent enzymatic reaction, particularly with saccharides, isomerizing aldoses and ketoses by transferring a phosphate from one position to another.

Another situation is where a composition is introduced into the solution which acts as an inhibitor or quencher of the emission of light, either by fluorescence or by chemiluminescence. For example, certain fluorescers are inhibited by superoxide. By employing superoxide dismutase to react with superoxide, the localized concentration of superoxide will be reduced, thus reducing the degree of quenching in the area of the signal producing enzyme.

As a further example, one could produce a fluorescent material from a nonfluorescent material, for example by having one of the functionalities substituted, so as to inhibit fluorescence. The example of umbelliferone has been indicated previously, but in this case a substituent is attached to the hydroxyl which requires only one enzyme for removal. The appropriate enzyme would then remove the substituent. The resulting umbelliferone would be activated by irradiation with light with the signal producing label being a fluorescent quencher which would accept energy from the excited umibelliferone by dipole-dipole interaction and reemit the light at a longer wave length. Nonenzymatic catalysis can also be employed, though generally not being employed as the reactant label. However, suitable catalysts include phenazine methosulfate, Meldola blue, FMN, methylene blue, pyocyanine, Wurster's blue, and 1,2-naphthoquinone. For example, Meldola blue, as reactant label, can serve to catalyse the reduction of FMN to $FMNH_2$ by NADH. The $FMNH_2$, can then react with bacterial luciferase as the signal producing label to give chemiluminescent emission.

Another situation is where the reactant label reacts with a compound in solution to produce a compound which can emit light. For example, bis-(dinitrophenyl) oxalate can be conveniently conjugated and upon reaction with hydrogen peroxide and base will form dioxetanedione. Dioxetanedione will decompose without the emission of light, unless it is in proximity to an acceptor molecule which will become electronically excited by the energy released by the decomposition and emit the light as chemiluminescence. Dioxetanedione has a sufficiently long half-life, so that it would be able to migrate to the quencher and does not require the quencher to be within a few angstroms of the dinitrophenyl oxalate.

Of particular interest are enzymatic reactant labels which react with a substrate by oxidizing an oxygen containing functionality to a higher oxidation state e.g. alcohol to ketone or aldehyde to carboxylic acid, or transfer a phosphate group inter- or intramolecularly by hydrolysis, phosphorylation or isomerization.

Signal Producing Label

As is evident from the discussion concerned with the reactant label, the signal producing label will vary widely as to its chemical composition, function, and nature of interaction with the signal mediator. As with the reactant label, it is desirable that the signal producing label be able to produce a plurality of events rather than a single event. The plurality of events can be as a result of catalytic reactions, energy transfer, absorption and reemission of light, electrochemical activity and the like.

As for catalytic reactions, the catalyst may be enzymatic or nonenzymatic. The enzymatic signal producing label will be coupled with reactant labels, particularly reactant labels which are in themselves enzymes. Thus, the product of the reactant label can act as the substrate of the signal producing label. For example, NAD produced from NADH or NADH produced from NAD or the phosphate analogs may be used by the signal producing label to react with a substrate to produce a signal, either absorption or emission of light. Examples of such enzymes include diaphorase, dehydrogenases, flavoproteins, cuproproteins, hemes, and the like. Another group of enzymes are those which react with hydrogen peroxide, such as peroxidase. Peroxidase can react with luminol and hydrogen peroxide to produce chemiluminescence.

The use of hydrolases has already been discussed in relation to the reactant label. The hydrolases can remove the second functionality so as to release a compound which has desirable absorption or emission characteristics.

Alternatively, these signal producing labels may be an nonenzymatic catatlyst, a number of catalysts having been described previously. These catalysts would then catalyze the reaction between the product of the reactant label and a compound in solution. For example, Meldola blue can be used to catalyze the reaction between NADH and tetrazolium salts.

As a further illustration, an energy acceptor compound may be employed, such as a dye, where the product of the reactant label is either a fluorescer formed in either its ground or excited state or an energy rich intermediate capable of exciting the acceptor compound. Energy would be transfered to the energy acceptor or quencher and emitted at a longer wave length which could be monitored.

Finally, the signal producing label can be a fluorescer which is quenched by a compound, such as superoxide. By reducing the concentration of superoxide in the presence of the fluorescer enhanced fluorescence can be observed.

Of particular interest are oxidoreductase enzymes, and of these, those enzymes which are NAD dependent. The increase or reduction in the concentration of NADH is particularly useful as the detectable signal. The NADH as the signal producing agent can be determined spectrophotometically by absorption or fluorescent emission.

Signal Mediator

The signal mediator acts as a regulator of a signal which results from the signal mediators interaction in the signal producing system. For the most part, the signal mediator will not produce the observed signal. The primary exception is where the signal mediator is a product of the reactant label and reacts with a product of the signal producing label to produce an observable signal. For example, one could have two compounds, which react rapidly together e.g. NADH and Meldola blue. By monofunctionalizing the Meldola blue and by having appropriate enzymes as the reactant label and the signal producing label to remove the functionality from the Meldola blue and produce NADH from NAD, the two reactants will be produced. In the presence of a tetrazolium salt, one can follow the reaction of NADH and Meldola blue by the formation of formazan.

The signal mediator can be a wide variety of compounds, including such compounds as coenzymes, fluorescers, catalysts, chemiluminescers, reductants, oxidants, inhibitors, and the like. That is, almost any compound whose concentration can be modified by chemical means and which is able to react with another compound, either chemically or electronically, to provide a detectable signal, either directly or indirectly.

There are a number of compounds -chromophores and chemiluminescers- which by themselves or by appropriate functionalization e.g. substitution with an enzymatically removable group, may serve as signal mediator precursors, signal mediators or as signal producing labels, which compounds or their products have the ability to become electronically excited by a chemical reaction and emit light or transfer energy (chemiluminescent) or to accept energy from radiation or an excited molecule and emit light at a longer wave length than the absorbed energy.

In the transfer of energy, it is desirable that there be a high efficiency of energy transfer from the energy donor to the energy acceptor. Desirably the energy donor will either be a chemiluminescer or a chromophore which absorbs light at wavelengths longer than 350 A°, preferably longer than 400 A°. Desirably, the acceptor chromophore will have an extinction coefficient greater than $10^4$ above 400 A°, preferably greater than $10^4$ above 450 A° and more preferably greater than $10^5$ above 400 A°.

As illustrative of the use of chromophores and light emission as the detectable signal are the following examples. HRP can react with acetone and hydrogen peroxide to yield triplet acetone (signal mediator) which migrates to 9,10-dibromoanthracene (signal producing label) which will accept energy from the triplet acetone and fluoresce.

A chemiluminescent reagent could be provided which reacts with the reactant label to produce the reagent in an excited state, which in turn would transfer energy to and excite a chromophore in solution. The excited chromophore (signal mediator) would then migrate to an energy acceptor (signal producing label) which would accept the transfer of energy through collison or dipole-dipole coupling and in turn fluoresce to produce a detectable signal.

As illustrative of various chromophores which may find use and are fluorescers are the following compounds and families of compounds.

The first family of fluorescers are the xanthene dyes, which include the fluoresceins derived from 3,6-dihydroxy-9-phenylxanthhydrol. The rhodamines and fluoresceins have a 9-o-carboxyphenyl group and are derivatives of 9-o-carboxyphenylxanthhydrol.

These compounds are commercially available with substituents on the phenyl group which can be used as the site for bonding or as the bonding functionality. For example, amino and isothiocyanate substituted fluorescing compounds are available.

Other dyes which are fluorescent include 3-phenyl-7-isocyanatocourmarin, acridines, such as 9-isothiocyanatoacridine and acridine orange; N-(p(2-benzoxazolyl)phenyl) maleimide; benzoxadiazoles, such as 4-chloro-7-nitrobenzo-2-oxa-1,3-diazole and 7-(p-methoxybenzylamino)-4-nitrobenzo-2-oxa-1,3-diazole; stilbenes, such as 4-dimethylamino-4'-isothiocyanatostilbene and 4-dimethylamino-4'-maleimidostilbene; N,N'-dioctadecyloxy carboxyanine p-toluenesulfonate; pyrenes, such as 8-hydroxy-1,3,6-pyrenetrisulfonic acid, and 1-pyrenebutyric acid; merocyanines e.g. merocyanine 540, rose bengal, 2,4-diphenyl-3(2H)-furanone; cyanines; anthraquinones; porphyrins; triarylmethanes; as well as other readily available dyes which are capable of fluorescing. These dyes, either have active funtionalities for conjugation or such functionalities may be readily introduced.

It should further be noted that the absorption and emission characteristics of the dye may vary from being free in solution and being bound to a protein or ligand. Therefore, when referring to the various wave length ranges and characteristics of the dyes, it is intended to indicate the dyes as employed and not the dye which is unconjugated and characterized in an arbitrary solvent. In the area of overlap between the fluorescer or chemiluminescer and acceptor or quencher, it is desirable that the acceptor should have a high transition probability.

The chemiluminescent source may be the reactant label, or involve a reagent reacting with the reactant label or the signal mediator, and may rarely be the signal producing label. The chemiluminescent source involves a compound which becomes electronically excited by a chemical reaction and may then emit light which serves as the detectable signal or donates energy to an acceptor which emits light as the detectable signal or in turn acts as a donor to a second acceptor which emits light as the detectable signal.

The chemiluminescent source may have a single component or a plurality of components, usually two or three components. While it is feasible that there be a single molecule which is thermally labile and on decomposition chemiluminesces, such as certain dioxetanes, for a number of reasons the use of these molecules will not be commercially practical. Therefore, for the most part, the chemiluminescent source will have at least two components and the major portion of the discussion will be directed to this situation.

For purposes of convenience, the chemiluminescent source will be divided into two categories; those which do not involve the intermediacy of enzyme catalysis; and those which do involve enzyme catalysis.

Considering chemiluminescence sources which do not involve enzyme catalysis, only those sources can be employed which chemiluminesce under conditions which either do not inhibit the binding of the receptor to the ligand, or do not degrade the receptor and ligand at an unacceptable rate during the period of measurement. While ordinarily, chemiluminescent sources which are dependent upon nonaqueous solvents and strong basic conditions, greater than pH11, will not be useful, techniques can be employed involving rapid injections or flow techniques where the modulated emission is substantially completed before the protein is denatured and significant dissociation occurs. After injection of base, one would observe a burst of light which could be measured.

A diverse number of families of compounds have been found to provide chemiluminescence under a variety of conditions. One family of compounds is 2,3-dihydro-1,4-phthalazinediones. The most popular compound is luminol which is the 5-amino compound. Other members of the family include the 5-amino-6,7,8-trimethoxy and the dimethylamino[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino and -methoxy substituents.

The next group of compounds is based on chemiluminescers which chemiluminesce under enzymatic catalysis. Primarily, there are two groups of enzymatically catalyzed chemiluminescers. The first group is those compounds which chemiluminesce in combination with alkaline hydrogen peroxide. By employing a peroxidase e.g. horse radish peroxidase in combination with hydrogen peroxide and the chemiluminescer, chemiluminescence can be achieved. Illustrative systems include 2,3-dihydro-1,4-phthalazinediones.

The second enzymatic source of chemiluminescence is based on luciferins and their analogs and luciferases. Of particular importance are bacterial luciferases.

The next group of chemiluminescent compounds are indolen-3-yl hydroperoxides, precursors thereto and derivatives thereof.

The next group of compounds is the bis-9,9'-biacridinium salts, of which lucigenin, N,N'-dimethyl-9,9'-biacridinium dinitrate is illustrative. These compounds chemiluminesce upon combination with alkaline hydrogen peroxide.

The next group of compounds is acridinium salts which are substituted in the 9 position. Particular substituents are carboxylic esters, particularly the aryl esters, acyl substituents, particularly benzoyl, and cyano. Alkaline hydrogen peroxide is employed to induce chemiluminescence.

Another group of compounds is various acyl peroxy esters and hydroperoxides, which may be formed in situ, in combination with compounds such as 9,10-diphenylanthracene.

Another source of chemiluminescence is hydroperoxides e.g. tetralin hydroperoxide, in combination with metal complexes, particularly porphyrins and phthalocyanines, where the metals are iron and zinc.

Preferred systems are those which provide a satisfactory quantum efficiency of emission from the chemiluminescer at a pH at or below 11, preferably at or below 10, and, furthermore, rely on a catalyst which may be conjugated to a member of the specific binding pair.

In view of the varied systems which may be employed as labels and signal modifiers, no simple definition is available as to the chemical and/or physical nature of the various materials. However, certain combinations will be preferred. While the following list is not intended to be exhaustive, it will indicate general categories of desirable combinations. The first category involves the use of at least one enzyme.

These combinations include an oxidoreductase enzyme as the reactant label, a coenzyme e.g. NAD or derivative (reduced and/or phosphate), and a second enzyme as the signal producing label which employs the form of the coenzyme produced by the first enzyme.

A second system employs an oxidoreductase enzyme as the reactant label which produces hydrogen peroxide as the signal mediator and a second enzyme which is also an oxidoreductase, particularly a peroxidase, which reacts with the hydrogen peroxide and an ancillary substrate such as a dye precursor or a chemiluminescent compound, such as luminol, to produce light.

A third variant is the employment of an oxidoreductase enzyme which reacts with a coenzyme e.g. NAD to produce NADH, which serves as a signal mediator, which then reacts with a dye in a catalysed reaction, where the catalyst is nonenzymatic and is the signal producing label.

A fourth variant is where both labels are hydrolase enzymes and a fluorescer or chemiluminescer is disubstituted with substituents which are individually removed by the enzymes. The mono-substituted compound is the signal mediator. Other systems may come readily to mind.

The following is an illustrative table of various systems which may be employed in accordance with the subject invention.

| REACTANT LABEL[1] | SIGNAL MEDIATOR[2] | SIGNAL PRODUCING LABEL[3] | REACTION SCHEME[4] |
|---|---|---|---|
| 1. PGI | G-6-P | G6PDH | F-6-P $\xrightarrow{PGI}$ G-6-P    NADPH $\xrightarrow{h\nu}$ NADPH* <br> G-6-P $\xrightarrow{G6PDH}$ GL-6-P    NADPH* $\longrightarrow$ NADPH + $h\nu'$ <br> NADP ⇌ NADPH |
| 2. AP | 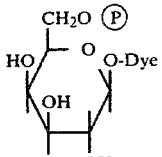 | β-G |  |
| 3. NAD—DH | NADH | PMS or MB | $RH_2 \xrightarrow{NAD-DH} R$   NADH + INT $\xrightarrow{PMS\ or\ MB}$ NAD + Formazan <br> NAD ⇌ NADH |
| 4. GO | $H_2O_2$ | HRP | Glucose + $O_2 \xrightarrow{GO} H_2O_2$ + glucuronate <br> $H_2O_2$ + luminol $\xrightarrow{HRP}$ $h\nu$ |
| 5. β-G | tridecanal | LF | $C_{12}H_{25}CH-O$ [sugar] $\xrightarrow{\beta\text{-}G}$ $C_{12}H_{25}CHO$ + FMNH $\xrightarrow{LF}$ $h\nu$ <br> F—N ORase <br> FMN + NADH |
| 6. MDH | PMS | β-G | malate $\xrightarrow{MDH}$ oxaloacetate   NADH + INT $\xrightarrow{PMS}$ Formazan <br> NAD ⇌ NADH <br> [sugar]-OCO(N . PMS) $\xrightarrow{\beta\text{-}G}$ PMS |
| 7. HRP | 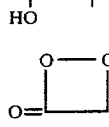 | Br-anthracene-Br (DiBrA) | $(CH_3)_2CHCHO \xrightarrow{HRP}$ [dioxetane] $\xrightarrow{DiBrA}$ $h\nu$ |
| 8. ($O_2N$-⟨⟩-OCO)₂ NO₂ (2,4-DPO) | [dioxetanedione] | fluorescein | 2,4-DPO + $H_2O_2 \longrightarrow$ [dioxetanedione] <br> [dioxetanedione] + fluorescein $\longrightarrow$ fluorescein* $\longrightarrow$ $h\nu$ |

-continued

| REACTANT LABEL[1] | SIGNAL MEDIATOR[2] | SIGNAL PRODUCING LABEL[3] | REACTION SCHEME[4] |
|---|---|---|---|
| 9. AP | G6P | G6PDH | 6(P)-β-glucosyl-(P) $\xrightarrow{AP}$ G6P <br> G6P $\xrightarrow{G6PDH}$ GL-6-P <br> NAD → NADH |
| 10. TIM | HOCH$_2$COCH$_2$O(P) (DiHAP) | α-GDH | (P)OCH$_2$CHOHCHO $\xrightarrow{TIM}$ DiHAP <br> DiHAP $\xrightarrow{\alpha\text{-GDH}}$ glyceryl-(P) <br> NADH → NAD |
| 11. AP | DiHAP | α-GDH | (P)OCH$_2$COCH$_2$O(P) $\xrightarrow{AP}$ DiHAP <br> DiHAP $\xrightarrow{\alpha\text{-GDH}}$ α-glyceryl-(P) <br> NADH → NAD |
| 12. AP | (P)OCH$_2$CHOHCHO | TIM | (P)OCH$_2$CHOHCH(OMe)O(P) $\xrightarrow{AP}$ (P)OCH$_2$CHOHCHO <br> (P)OCH$_2$CHOHCHO $\xrightarrow{TIM}$ DiHAP <br> DiHAP $\xrightarrow{\alpha\text{-GDH}}$ Glyceryl-(P) <br> NADH → NAD |
| 13. Hexokinase | G6P | G6PDH | glucose $\xrightarrow{Hexokinase}$ G6P <br> ATP → ADP <br> G6P $\xrightarrow{G6PDH}$ GL-6-P <br> NAD → NADH |
| 14. PGM | G6P | G6PDH | α-glucose-1-(P) $\xrightarrow{PGM}$ G6P <br> G6P $\xrightarrow{G6PDH}$ GL-6-P <br> NAD → NADH |
| 15. PK | Pyruvate | LDH | PEP $\xrightarrow{PK}$ Pyruvate <br> ADP → ATP <br> Pyruvate $\xrightarrow{LDH}$ lactate <br> NADH → NAD |
| 16. β-G | fluorescein | umbelliferone | di(β-galactosidyl)fluorescein $\xrightarrow{\beta\text{-G}}$ m-(β-G)fluorescein <br> umbelliferone $\xrightarrow{h\nu}$ umbelliferone* <br> umbelliferone* + m-(β-G)fluorescein ⟶ m-(β-G)fluorescein* + umbelliferone <br> m-(β-G)fluorescein* ⟶ m-(β-G)fluorescein + hν' |

| REACTANT LABEL[1] | SIGNAL MEDIATOR[2] | SIGNAL PRODUCING LABEL[3] | REACTION SCHEME[4] |
|---|---|---|---|
| 17. β-G | fluorescein | HRP | di(β-galactosidyl)fluorescein $\xrightarrow{\beta\text{-}G}$ m-(β-G)fluorescein <br><br> luminol + $H_2O_2$ $\xrightarrow{HRP}$ luminol* <br><br> luminol* + m-(β-G)fluorescein $\longrightarrow$ m-(β-G)fluorescein* + luminol <br><br> m-(β-G)fluorescein* $\longrightarrow$ m-(β-G)fluorescein + hν |

[1] PGI phosphoglucose isomerase
AP alkaline phosphatase
NAD—DH nicotinamide adenine dinucleotide-dependent dehydrogenase (I.U.B. Class 1.1.1)
GO glucose oxidase
β-G β-galactosidase
MDH malate dehydrogenase
HRP horse radish peroxidase
TIM triose phosphate isomerase
PGM phosphoglucomutase
PK pyruvate kinase
[2] G6P glucose-6-phosphate
Dye fluorescing chromophore having an hydroxyl, particularly phenolic e.g. fluorescein, hydroxycumarol, etc.
NADH nicotinamide adenine dinucleotide (reduced)
PMS phenazine methosulfate
DHAP dihydroxyacetone phosphate
[3] G6PDH glucose-6-phosphate dehydrogenase
β-G β-galactosidase
PMS phenazine methosulfate
MB Medola blue
HRP horse radish peroxidase
LF bacterial luciferase
DiBrA 9,10-dibromoanthracene
α-GDH α-glycerophosphate dehydrogenase
TIM triose phosphate isomerase
LDH lactate dehydrogenase
[4] F-6-P fructose-6-phosphate
NADP(H) nicotinamide adenine dinucleotide phosphate (reduced)
$RH_2$ substrate, usually having CHOH group, for a dehydrogenase
INT triaryltetrazolium chloride
Formazan triarylformazan
FMN flavin monnucleotide
F—N ORase FMN—NADH oxidoreductase
N—PMS N-substituted phenazine methosulfate
LDH lactate dehydrogenase
α-GDH α-glycerophosphate dehydrogenase
GL-6-P 6-P-glucuronate
PEP phosphoenolpyruvate
*excited state
m-(β-G) mono-(β-galactosidyl)

Conjugates

The conjugates—reactant label and/or signal producing label bonded to a member of the specific binding pair—may involve covalent or non-covalent, usually covalent bonding, of the label to the specific binding pair member. The various covalent linking groups have been discussed previously in conjunction with the ligand analog.

Where two molecules are to be conjugated, one small ($\leq 1000$ m.w.) and the other large ($\geq 1000$, usually $\geq 5,000$ m.w.), the smaller molecule is usually provided with a functionality capable of reacting with functionalities naturally present in the large molecule. However, where two large molecules are involved, particularly those having the same active functionalities e.g. proteins, a difunctional linking group or carboxyl activating compounds e.g. carbodiimides, will be employed, or each of the compounds may be functionalized with different functionalities which react with each other e.g. maleimide and mercapto.

The molecules may be joined together in accordance with known synthetic techniques.

Where ligands are small molecules ($\leq 1000$ m.w.), the number of ligands conjugated to a large molecule ($\leq 5,000$ m.w.), will be on the average at least one ligand per label and not more than about one ligand per 1,500, usually per 2,500, molecular weight of label. Where both the molecules to be conjugated i.e. ligand and label or receptor and label, are large there will generally be on the average at least one of each of the members of the conjugate and there may be as many as ten or more of one or each of the members.

The next consideration is a special situation where the reactant label and the signal producing label are the same, normally an enzyme. This requires a special signal mediator precursor. The precursor is either monosubstituted with an oligomer, usually having at least 2 units, more usually 2 units, which has a repeating unit joined by a functionality cleaved by the label or has a plurality of substituents, usually at least 2, more usually 2, bonded at different sites, by functionalities cleaved by the label, where the signal mediator is at some intermediate level of substitution. Examples are di- or polysaccharides, di- or polyphosphates, di- or poly(amino acids), and the like.

The signal mediator precursor is therefore substituted in such a way that at least two bonds must be cleaved to obtain a detectable signal and the bonds are all cleavable by the same enzyme. The enhancement in rate is due to the higher localized concentration of the enzyme label and signal mediator in the microenvironment as well as the restrictions on the diffusion of the signal mediator away from the microenvironment.

Labels of particular interest are saccharidases e.g. galactosidase, in combination with the appropriately saccharide substituted signal mediator precursor.

The following examples are offered by way of illustration and not by way of limitation.

EXPERIMENTAL (All temperatures not otherwise indicated are in centigrade. All parts and percents not otherwise indicated are by weight, except where mixtures of liquids are involved and are then by volume. The following abreviations will be employed: HRP-horse radish peroxidase; GO- galactose oxidase; FDNB - fluorodinitrobenzene, hIgG - human γ-globulin.).

EXAMPLE 1.

Conjugation of HRP to goat anti(hIgG)

The procedure employed follows that taught by Nakane and Kawaoi, J. Histochem. and Cytochem. 22, 1,084 (1974).

In 2 ml of freshly prepared phosphate buffer (0.3 M,pH 8.1) was dissolved 12.3 ml of HRP and 0.25 ml of FDNB added and the mixture allowed to stand for one hour. After withdrawing about 1 ml, 1.2 ml of 0.04 M periodate was added to the remaining 1 ml and the mixture stirred for about 0.5 hr at room temperature. To the mixture was then added 1.2 ml of ethylene glycol. The mixture was then dialyzed against buffer. To the residue in the dialysis bag was added 600 ml of goat anti(hIgG) (Miles Laboratories) and the mixture stirred for 3 hrs at room temperature. To the mixture was then added 9 mg sodium borohydride and the resulting reaction mixture allowed to stand at 4° overnight with stirring. The reaction mixture was then dialyzed against PBS, followed by chromatographing on a Sephadex G200 column employing PBS, pH 7.2 as eluant. The fractions eluted from the column were monitored by absorption at 403 nm and 276 nm, which together are diagnostic of the ratio of HRP and IgG respectively. The desired product was eluted in the early fractions.

EXAMPLE 2

Conjugation of GO to hIgG.

Into 1 ml of sodium bicarbonate buffer (0.3 M, pH 8.1) was introduced 2 mg hIgG and 6 mg GO, followed by the addition of 1 ml of 0.04 M sodium periodate. After one hr at room temperature, the mixture was diluted to 10 ml and concentrated on Diaflo Ultrafilter to 1 ml. To the mixture was added 3 ml sodium borohydride and after standing overnight, 10 ml of PBS pH7 was added. After concentrating to 1 ml with a Diaflo Ultrafilter the mixture was chromatographed on a 0.3×45 cm Sephadex G200 column. Employing PBS pH7.2 buffer as eluant, the fractions were monitored with a uv spectrophotometer, monitoring the absorption at 280 nm.

In order to demonstrate the subject invention, the following experiments were carried out. A plurality of tubes of different concentrations were prepared. The following table indicates the composition of the reaction media.

TABLE I

| Material | Conc. M | Tube: | 1 | 2 | 3 | 4 | 5 | 6 | 7 |
|---|---|---|---|---|---|---|---|---|---|
| HRP—Ab$_{hIgG}$[a] | $3 \times 10^{-8}$ | | 10 | 10 | 10 | 10 | 10 | 10 | 10 |
| hIgG | $1.6 \times 10^{-6}$ | | 5 | 2.5 | | | | | |
|  | $1.6 \times 10^{-7}$ | | | | 5 | 2.5 | | | |
|  | $1.6 \times 10^{-8}$ | | | | | | 5 | 2.5 | |
| hIgG—GO[b] | $3 \times 10^{-8}$ | | 5 | 5 | 5 | 5 | 5 | 5 | 5 |
| Buffer[c] | | | 0 | 2.5 | 0 | 2.5 | 0 | 2.5 | 0 |
| G/L[d] | | | 5 | 5 | 5 | 5 | 5 | 5 | 5 |

[a]Ex. I
[b]Ex. II
[c]pH9, Tris $5 \times 10^{-2}$M
[d]$0.5 \times 10^{-3}$M luminol, 6% galactose The total volume for all the tubes is 25 ml. The materials were added in the order indicated and the mixture incubated for 34 min at room temperature prior to addition of the G/L solution. Readings were then taken at a number of different times on a Beckman β-mate in the non-coincidence mode, the following table indicating the observed results.

TABLE II

| Time (min) | Tube: | Counts per 0.2 min × 10⁻³ ||||||
|---|---|---|---|---|---|---|---|---|
|  |  | 1 | 2 | 3 | 4 | 5 | 6 | 7 |
| 10 |  | 4 | 10 | 9 | 33 | 132 | 33 | 119 |
| 18 |  | 4 | 10 | 11 | 78 | 281 | 121 | 523 |
| 30 |  | 4 | 11 | 41 | 221 | 749 | 344 | — |
| 44 |  | 3 | 14 | 212 | 630 | 807 | 873 | 1011 |
| 56 |  | — | — | 540 | 855 | 900 | 940 | 1061 |
| 75 |  | 3 | 42 | 704 | 890 | 900 | 965 | 1080 |
| 95 |  | 3 | 203 | 810 | 902 | — | 1007 | 1117 |
| 115 |  | 3 | 340 | 800 | — | — | 980 | 1095 |

The above results are predicated on the HRP-anti(-hIgG) binding to the hIgG-GO to form a complex, where the peroxide produced by the reactant label-glucose oxidasecan act as a signal mediator with the signal producing label- horse radish peroxidase-and luminol to produce a chemiluminescence signal. In the absence of free hIgG, by providing for appropriate ratios of the HRP-anti(hIgG) and hIgG-GO conjugates, one can optimize the observed signal. By addition of hIgG to the medium, the signal will be diminished.

While it is believed that the ratio employed above is not the optimum ratio, the results are convincing that as one reduces the amount of hIgG added, the observed signal increases. This is particularly evident at about 45 min and continues to remain so thereafter. There would appear to be some discrepancy in the 30 min reading of tube 6, which discrepancy is unexplained. Nevertheless, the differences in the readings are quite dramatic over a 200 fold change in concentration in the hIgG.

The subject invention provides for a number of advantages in the determination of ligands. The method provides for high sensitivity, since a single ligand can affect a plurality of measureable events. Secondly, since the assay is predicated on bringing two different materials together in propinquity, labels which are conjugated to other than members of the specific binding pair will not significantly interfere. These extraneous labels will be free in solution and will not be significantly involved in the microenvironment created by the binding of the specific binding pair. Therefore, by appropriate choice of labels, where either the ligand or antiligand can only be obtained in relatively impure form, one can diminish the background effect when labelling the impure composition of ligand or antiligand.

The subject method has substantial flexibility in allowing for a wide variety of combinations, which can be employed to obviate endogenous interferences in the sample source. In addition, by employing a rate mode, one can carry out the assay over relatively short periods of time, since extremely sensitive counters can be employed, such as scintillation counters.

Although the foregoing invention has been described in some detail by way of illustration and example for purposes of clarity of understanding, it will be obvious that certain changes and modifications may be practiced within the scope of the appended claims.

What is claimed is:

1. A method for determining the presence of an analyte in a sample suspected of containing said analyte, said analyte being a member of a specific binding pair consisting of ligand and antiligand, wherein the amount of a detectable signal is a function of the amount of analyte in an assay medium, said detectable signal being produced by having three primary reagents:
    (A) reactant label conjugate consisting of a reactive organic compound conjugated to a member of said specific binding pair which interacts with a signal mediator precursor to produce a signal mediator;
    (B) signal producing label conjugate, which consists of a compound which is a component of a detectable signal producing system conjugated to a member of said specific binding pair, wherein the amount of signal produced is affected by the localized concentration of said signal mediator, with the proviso that said signal producing label and said reactant label may be bonded to the same molecular member of said specific binding pair to produce a single reagent which is a reactant label-signal producing label conjugate; and
    (C) signal mediator precursor, which is an unconjugated compound which interacts with said reactant label to produce said signal mediator which is said precursor in an electronically excited state or a reaction product of said signal mediator precursor and said reactant label, with the proviso that when said reactant label and said signal producing label are both the same enzyme, said signal mediator precursor has a plurality of substituents having bonds cleavable by said enzyme and said signal mediator is at an intermediate level of substitution by said substituents.

wherein the average spatial proximity in said assay medium of said reactant label and said signal producing label is affected by the concentration of analyte in said medium and the bringing together of said reactant label conjugates and said signal producing label conjugates or a plurality of reactant label-signal producing label conjugates by means of the binding together of said ligand or ligand analog and antiligand brings said reactant labels and said signal producing labels into a microenvironment, so as to create a localized concentration of signal mediator differing from the concentration of signal mediator in the mass of said assay medium;

said method comprising:
    combining in an aqueous assay medium:
        (A) said sample;
        (B) said reactant label conjugate;
        (C) said signal producing label conjugate; with the proviso that both said reactant label conjugate and signal producing label conjugate may be replaced with reactant label-signal producing label conjugate;
        (D) said signal mediator precursor with the proviso that when said reactant label and said signal producing label are both the same enzyme, said signal mediator precursor is employed having at least two substituents having covalent bonds cleaved by said enzyme;
        (E) any auxiliary reagents necessary for the reaction of said reactant label and said signal producing label; and
        (F) poly(ligand analog), when said ligand is mono-epitopic and monolabel-monoligand is employed as one of said conjugates; and
    determining the resulting detectable signal as compared to the detectable signal from an assay medium having a known amount of analyte.

2. A method according to claim 1, wherein the pH of said medium is in the range of about 4–11 and the temperature of said medium is in the range of about 10°–50° C.

3. A method according to claim 2, wherein said reactant label conjugate has an enzyme as said reactant label.

4. A method according to claim 3, wherein said enzyme is an oxidoreductase.

5. A method according to claim 4, wherein said oxidoreductase is a NAD dependent dehydrogenase.

6. A method according to claim 3, wherein said enzyme is a hydrolase.

7. A method according to claim 6, wherein said hydrolase is a phosphatase.

8. A method according to claim 6, wherein said hydrolase is a glycosidase.

9. A method according to claim 3, wherein said enzyme is an isomerase.

10. A method according to claim 2, wherein said signal producing label is an enzyme.

11. A method according to claim 10, wherein said enzyme is an oxidoreductase.

12. A method according to claim 11, wherein said oxidoreductase is a peroxidase.

13. A method according to claim 11, wherein said oxidoreductase is a NAD dependent dehydrogenase.

14. A method according to claim 10, wherein said enzyme is a hydrolase.

15. A method according to claim 14, wherein said hydrolase is a glycosidase.

16. A method according to claim 2, wherein said signal producing label is a fluorescer.

17. A method according to claim 2, wherein said signal producing label is a nonenzymatic catalyst.

18. A method according to claim 2, wherein said analyte is an antigen.

19. A method according to claim 18, wherein said antigen is a globulin.

20. A method according to claim 18, wherein said antigen is a hormone.

21. A method according to claim 18, wherein said antigen is a viral protein.

22. A method according to claim 2, wherein said analyte is a hapten.

23. A method according to claim 22, wherein said hapten is a steroid.

24. A method according to claim 22, wherein said hapten is an alkaloid.

25. A method according to claim 22, wherein said hapten is a synthetic drug.

26. A method for determining the presence of a ligand in a sample suspected of containing said ligand, said ligand being a member of a specific binding pair consisting of ligand and antiligand, wherein the amount of a detectable signal is a function of the amount of analyte in an assay medium, said detectable signal being produced by having three primary reagents:
  (A) reactant label conjugate consisting of first enzyme conjugated to a member of said specific binding pair, wherein said enzyme reacts with a signal mediator precursor to produce a signal mediator;
  (B) signal producing label conjugate, which consists of a second enzyme, which is a component of a detectable signal producing system, said second enzyme being conjugated to a member of said specific binding pair, wherein the amount of signal produced is affected by the localized concentration of said signal mediator; and
  (C) signal mediator precursor, which is an unconjugated compound which reacts with said first enzyme to produce, said signal mediator, which reacts with a product of said second enzyme or said second enzyme to produce said detectable signal;
wherein the spatial proximity in said assay medium of said reactant label conjugate and said signal producing conjugate is affected by the concentration of ligand in said medium and the bringing together of said reactant label conjugate and said signal producing label conjugate by means of the binding together of said ligand or ligand analog and antiligand, brings said reactant label and said signal producing label into close spatial proximity in a microenvironment, so as to create a localized concentration of signal mediator differing from the concentration of signal mediator in the mass of said assay medium;
said method comprising:
combining in an aqueous assay medium:
  (A) said sample;
  (B) said reactant label conjugate;
  (C) said signal producing label conjugate;
  (D) said signal mediator precursor
  (E) any auxiliary reagents necessary for the reaction of said first and second enzymes;
  (F) poly(ligand analog), when said ligand is monoepitopic and monolabel-monoligand is employed as one of said conjugates; and
determining the resulting detectable signal as compared to the detectable signal from an assay medium having a known amount of analyte.

27. A method according to claim 26, wherein the pH of said assay medium is in the range of about 4–11 and the temperature of said assay medium is in the range of about 10°–50° C.

28. A method according to claim 27, wherein said first and second enzymes are oxidoreductases.

29. A method according to claim 28, wherein said first enzyme produces hydrogen peroxide and said second enzyme is a peroxidase.

30. A method according to claim 29, wherein said first enzyme is glucose oxidase and said detectable signal is produced by the reaction of peroxidase, hydrogen peroxide and a chemiluminescer.

31. In a kit, in combination peroxidase conjugated to antiligand and glucose oxidase conjugated to antiligand, where the antiligands bind to the same ligand, and the ratio of the two conjugates is selected to substantially optimize the production of a detectable signal in accordance with the method of claim 30.

32. A method according to claim 29, wherein said first enzyme is galactose oxidase and said detectable signal is produced by the reaction of peroxidase, hydrogen peroxide and a chemiluminescer.

33. In a kit, in combination peroxidase conjugated to antiligand and galactose oxidase conjugaed to antiligand, where the antiligands bind to the same ligand, and the ratio of the two conjugates is selected to substantially optimize the production of a detectable signal in accordance with the method of claim 32.

34. A method according to claim 32, wherein said ligand is an antigen.

35. A method according to claim 34, wherein said antigen is a globulin.

36. A method according to claim 34, wherein said antigen is a hormone.

37. A method according to claim 27, wherein said first enzyme is a hydrolase.

38. A method according to claim 27, wherein said second enzyme is a hydrolase.

39. A method according to claim 27, wherein said first enzyme is an isomerase.

40. A method according to claim 1 or 26, where the member of said specific binding pair in at least one of said reactant label conjugate and signal producing label conjugate is polyepitopic ligand or ligand analog and including the step of combining polyreceptor in said aqueous assay medium.

41. In a kit in combination, a first enzyme conjugated to antiligand and a second enzyme conjugated to antiligand, wherein the antiligands bind to the same ligand and the product of said first enzyme is the substrate of said second enzyme.

42. In a kit, in combination a (first enzyme)-bound-ligand and a (second enzyme)-bound-antiligand, where the antiligand binds to said (first enzyme)-bound-ligand and the products of said first and second enzymes react to produce a detectable signal.

43. In a kit, in combination a (first enzyme)-bound-ligand and a (second enzyme)-bound-antiligand, where the antiligand binds to said (first enzyme)-bound-ligand and the product of one of said enzymes reacts with the other of said enzymes to produce a detectable signal.

44. A method for determining the presence of a ligand which is human γ-globulin, wherein said human γ-globulin is a member of a specific binding pair consisting of human γ-globulin and anti(human γ-globulin), wherein the amount of a detectible signal is a function of the amount of human γ-globulin in an assay medium, said detectible signal being produced by having three primary reagents:
  (a) (human γ-globulin)-galactose oxidase conjugate;
  (b) anti(human γ-globulin)-horse radish peroxidase conjugate; and (c) galactose, which undergoes a catalyzed reaction by galactose oxidase to produce hydrogen peroxide;

wherein the spatial proximity in said assay medium of said human (γ-globulin)-galactose oxidase conjugate and said anti(human γ-globulin)-horse radish peroxidase conjugate is affected by the concentration of human γ-globulin in said medium, wherein when said (human γ-globulin)-galactose oxidase conjugate binds to said anti(human γ-globulin)-horse radish peroxidase conjugate, there results an enhanced concentration of hydrogen peroxide in the presence of said horse radish peroxidase differing from the concentration of hydrogen peroxide in the mass of said assay medium;

said method comprising:

combining in an aqueous assay medium:
  (a) said sample;
  (b) said (human γ-globulin)-galactose oxidase conjugate;
  (c) said anti(human γ-globulin)-horse radish peroxidase conjugate;
  (d) said galactose; and
  (e) luminol; and determining the light emitted from said assay medium as compared to an assay medium having a known amount of human γ-globulin.

* * * * *